US012758602B2

(12) United States Patent
Han et al.

(10) Patent No.: US 12,758,602 B2
(45) Date of Patent: Oct. 13, 2026

(54) ANTI-INFLAMMATORY COMPOSITION COMPRISING EPIMENDIUM KOREANUM NAKAI, POLYGALA TENUIFOLIA WILD, AND POLYPORUS UMBELLATUS FRIES EXTRACTS OR MIXTURE THEREOF AS ACTIVE INGREDIENT

(71) Applicant: Korea Research Institute of Chemical Technology, Daejeon (KR)

(72) Inventors: Hyoung-Yun Han, Daejeon (KR); Jung-Hwa Oh, Daejeon (KR); Seokjoo Yoon, Daejeon (KR); Se-Myo Park, Daejeon (KR); Mi-Sun Choi, Daejeon (KR); Soojin Kim, Daejeon (KR)

(73) Assignee: Korea Research Institute of Chemical Technology, Daejeon (KR)

( * ) Notice: Subject to any disclaimer, the term of this patent is extended or adjusted under 35 U.S.C. 154(b) by 322 days.

(21) Appl. No.: 18/279,975

(22) PCT Filed: Mar. 19, 2021

(86) PCT No.: PCT/KR2021/003418
§ 371 (c)(1),
(2) Date: Sep. 1, 2023

(87) PCT Pub. No.: WO2022/186414
PCT Pub. Date: Sep. 9, 2022

(65) Prior Publication Data

US 2024/0148810 A1 May 9, 2024

(30) Foreign Application Priority Data

Mar. 2, 2021 (KR) ........................ 10-2021-0027214

(51) Int. Cl.

| | |
|---|---|
| ***A61K 36/296*** | (2006.01) |
| ***A61K 36/07*** | (2006.01) |
| ***A61K 36/69*** | (2006.01) |
| ***A61P 29/00*** | (2006.01) |
| ***A61P 39/06*** | (2006.01) |

(52) U.S. Cl.
CPC ............ *A61K 36/296* (2013.01); *A61K 36/07* (2013.01); *A61K 36/69* (2013.01); *A61P 29/00* (2018.01); *A61P 39/06* (2018.01); *A61K 2236/331* (2013.01)

(58) Field of Classification Search
None
See application file for complete search history.

(56) References Cited

PUBLICATIONS

Chen (CN 106692856 A—English translation)—May 24, 2017.*
Tong (CN 104958668 A—English translation)—Oct. 7, 2015.*
Wei (CN 104147369—English translation)—Nov. 19, 2014.*
International Search Report and Written Opinion in PCT/KR2021/003418, issued by the Korean Search Authority of the Korean Intellectual Property Office, mailed on Jun. 9, 2022, 7 pages (with English translation of International Search Report and Written Opinion, 5 pages).
Jung et al., "Anti-inflammatory Effects of Epimedii Herba Water Extract through Inhibition of Nuclear Factor—κB in Raw 264.7 Cells," *Kor J Herbol.* 33.2: 19-28, 2018 (with Eng. translation of abstract).
Lee et al., "Effects of Polyporous Herbal-acupuncture at KI10 on LPS-induced nephritis in rats," *J Korean Med.* 36.3: 73-83, 2015 (with Eng. translation of abstract).
Oh and Kim, "Anti-inflammatory activity of the water extract of Polygala tenuifolia Willd," *Korean J Orient Int Med.* 34.2: 204-214, 2013 (with Eng. translation of abstract).
Oh et al., "Inhibitory Effects of Epimedium Herb on the Inflammatory Response In Vitro and In Vivo," *The American Journal of Chinese Medicine* 43.5: 1-16, 2015.
Son et al., "Inhibition of gene expression and production of iNOS and TNF-α in LPS-stimulated microglia by On-Bi-Tang," *Kor J Herbol.* 21.2: 135-142, 2006 (with Eng. translation of abstract).
Zeng, "The Effect of *Polyporus umbellatus* (Chinese medicine) on LPS-induced Viability and Cytokine Expression in Raw 264.7 cells," Event Abstract, $15^{th}$ International Congress of Immunology, Milan, Italy, Aug. 22-27, 2013 (1 page).
Guan, et al. "Majority of Chinese medicine herb category 'Qing Re Yao' have multiple mechanisms of anti-inflammatory activity," *Scientific Reports* 8(1):7416, May 2018 (11 pages).

* cited by examiner

*Primary Examiner* — Susan Hoffman
(74) *Attorney, Agent, or Firm* — Klarquist Sparkman, LLP

(57) ABSTRACT

The present invention relates to an anti-inflammatory composition comprising *Epimedium koreanum* Nakai, *Polygala tenuifolia* Willd, and *Polyporus umbellatus* Fries extracts or a mixture thereof as an active ingredient. The extracts and mixture prepared according to the present invention exhibit a high inhibitory effect against nitric oxide and a suppressive effect against the expression of iNOS and COX2 and thus can be advantageously used as an anti-inflammatory composition.

12 Claims, 7 Drawing Sheets

ANTI-INFLAMMATORY COMPOSITION COMPRISING EPIMENDIUM KOREANUM NAKAI, POLYGALA TENUIFOLIA WILD, AND POLYPORUS UMBELLATUS FRIES EXTRACTS OR MIXTURE THEREOF AS ACTIVE INGREDIENT

CROSS REFERENCE TO RELATED APPLICATIONS

This application is a U.S. National Stage application filed under 35 U.S.C. § 371 of International Application No. PCT/KR2021/003418, filed Mar. 19, 2021, which in turn claims the benefit of Korean Application No. KR 10-2021-0027214, filed Mar. 2, 2021. The Korean patent application is incorporated herein in its entirety.

BACKGROUND OF THE INVENTION

1. Field of the Invention

The present invention relates to an anti-inflammatory composition comprising natural extracts of *Epimedium koreanum* Nakai, *Polygala tenuifolia* Willd, and *Polyporus umbellatus* Fries or a mixture thereof as an active ingredient.

2. Description of the Related Art

Inflammation is a defense mechanism that prevents tissue damage caused by infection and is accompanied by symptoms such as fever and pain, and restores normal structure and function by removing pathogens and regenerating tissue.

However, if the antigen is not removed, or if the inflammatory response is excessive or persistent due to internal substances, it can promote mucosal damage and lead to various chronic diseases such as neurodegenerative diseases and cancer.

In the human immune response, macrophages are involved in and regulate the production of inflammatory mediators such as nitric oxide (NO), prostaglandin (PG) and pro-inflammatory cytokines, and the inflammatory mediators act as a defense mechanism in the body by inducing an inflammatory response. However, if the host's immune response fails to respond appropriately, inflammatory diseases may be induced.

On the other hand, substances that act to remove inflammatory sources, reduce biological responses and symptoms in order to disappear inflammation are called anti-inflammatory agents.

Substances currently used for the purpose of anti-inflammation include nonsteroids such as flufenamic acid, ibuprofen, benzydamine, and indomethacin, and steroids such as prednisolone, and dexamethasone. In addition, allantoin, azene, hydrocortisone, etc. are known to be effective in anti-inflammation, but there is a problem in that the amount of use is limited due to safety issues on the skin, or the effect is insignificant, so that a substantial anti-inflammatory effect cannot be expected. Therefore, efforts have been made to find components with antioxidant and anti-inflammatory activity from natural sources.

*Epimedium koreanum* Nakai is a perennial herbaceous plant belonging to Berberidaceae, and is also called a barrenwort. The rhizome extends sideways, has many fine roots, and scale-like leaves are surrounded under the main stem. The leaflets are ovoid, pointed at the end, 5-3.5 cm long, 1.5-7.2 cm wide, with fine sawtooth like hairs on the edge. The flowers are yellowish white and hang downward on the raceme at the end of the main stem, and the fruit is a follicle with a length of 10~13 mm and a diameter of 5~6 mm. In oriental medicine, it is known as *Epimedium koreanum* Nakai. It has the effect of dispelling wind and dampness, strengthening intellect, fortifying muscles and bones, and enhancing the body's vital energy. Therefore, it is used to treat conditions such as hemiplegia, muscle and bone atrophy, limb weakness, and urinary incontinence.

*Polygala tenuifolia* grows on the sunny side of low mountains in the north of central Korea. In autumn or spring, the roots are dug up and washed in water, then the woody parts are removed and dried in the sun. The taste is bitter and spicy, and warm in nature. In pharmacological experiments, it has been found that it has sedative, hypnotic, cardiac, expectorant, and hemolytic effects. It is used for heart palpitations while being surprised, forgetfulness, coughing with phlegm, furuncle, etc. It is also used for bronchitis. Take 3-9 g per day in the form of decoctions, pills, powders, and injections.

*Polyporus umbellatus* Fries is a kind of fungal plant that grows on the roots of maple, oak, birch, etc., and is a widely used herb in Chinese medicine. It contains elgosterol, biotin, proteins, and sugars as medicinal ingredients. In terms of pharmacological effects, taking 5 g of *Polyporus umbellatus* Fries decocted water increased urine output within 6 hours in healthy people, and also inhibited the growth of *Staphylococcus aureus* and *E. coli*. The medicinal properties of this drug are mediocre and the taste is plain.

As a medicinal effect, it has a significant diuretic effect, so when there is systemic edema due to nephritis, it removes the edema with a mild diuretic effect and reduces inflammation. In addition, it is often applied when there is pain in not being able to urinate due to cystitis or urethritis. It is used for diuretic purposes when edema is severe during pregnancy and when edema is accompanied by beriberi.

*Polygala tenuifolia* Willd and *Epimedium koreanum* Nakai each have been reported anti-inflammatory activity as a pharmacologic action. The ethanol extract of *Polygala tenuifolia* Willd exhibited anti-inflammatory activity, reduced iNOs and COX2 protein expression levels, and reduced edema in a carrageenan-induced acute paw edema rat model in vivo. *Epimedium koreanum* Nakai inhibited LPS-induced nitric oxide production in a concentration-dependent manner. However, since it did not suppress the expression levels of major inflammatory markers, it is considered that the overall activity is not strong as a result of anti-inflammatory activity studies on *Epimedium koreanum* Nakai components. In addition, since toxicity was observed in the histopathological results of repeated tests using rodents for *Polygala tenuifolia* Willd and *Epimedium koreanum* Nakai, it is difficult to use them as a single herbal anti-inflammatory composition.

As described above, each of *Epimedium koreanum* Nakai and *Polygala tenuifolia* Willd has been reported to have anti-inflammatory activity, but each substance has cytotoxicity and low anti-inflammatory activity. Accordingly, the present inventors have studied *Epimedium koreanum* Nakai, *Polygala tenuifolia* Willd, and *Polyporus umbellatus* Fries. As a result, the present inventors completed the present invention by confirming that the herbal anti-inflammatory composition of *Polygala tenuifolia* Willd, *Epimedium koreanum* Nakai, and *Polyporus umbellatus* Fries can be used as an anti-inflammatory composition by increasing anti-inflammatory activity and reducing toxicity through combination.

SUMMARY OF THE INVENTION

It is an object of the present invention to provide a pharmaceutical composition for the prevention or treatment of inflammatory diseases comprising *Epimedium koreanum* Nakai, *Polygala tenuifolia* Willd, and *Polyporus umbellatus* Fries extracts or a mixture thereof as an active ingredient.

It is another object of the present invention to provide a method for preparing a pharmaceutical composition for the prevention or treatment of inflammatory diseases, comprising the steps of extracting *Epimedium koreanum* Nakai, *Polygala tenuifolia* Willd, and *Polyporus umbellatus* Fries, concentrating the extracts, and lyophilizing the extracts.

It is another object of the present invention to provide a health functional food for the prevention or amelioration of inflammatory diseases comprising *Epimedium koreanum* Nakai, *Polygala tenuifolia* Willd, *Polyporus umbellatus* Fries extracts and a mixture thereof as an active ingredient.

To achieve the above objects, in an aspect of the present invention, the present invention provides a pharmaceutical composition for the prevention or treatment of inflammatory diseases comprising *Epimedium koreanum* Nakai, *Polygala tenuifolia* Willd, and *Polyporus umbellatus* Fries extracts or a mixture thereof as an active ingredient.

In another aspect of the present invention, the present invention provides a method for preparing a pharmaceutical composition for the prevention or treatment of inflammatory diseases, comprising the steps of extracting *Epimedium koreanum* Nakai, *Polygala tenuifolia* Willd, and *Polyporus umbellatus* Fries, concentrating the extracts, and lyophilizing the extracts.

In another aspect of the present invention, the present invention provides a health functional food for the prevention or amelioration of inflammatory diseases comprising *Epimedium koreanum* Nakai, *Polygala tenuifolia* Willd, *Polyporus umbellatus* Fries extracts and a mixture thereof as an active ingredient.

Advantageous Effect

The extracts and mixture provided in an aspect of the present invention exhibit a high inhibitory effect against nitric oxide and a suppressive effect against the expression of iNOS and COX2 and thus can be advantageously used as an anti-inflammatory composition.

DESCRIPTION OF THE PREFERRED EMBODIMENTS

Figure 1:
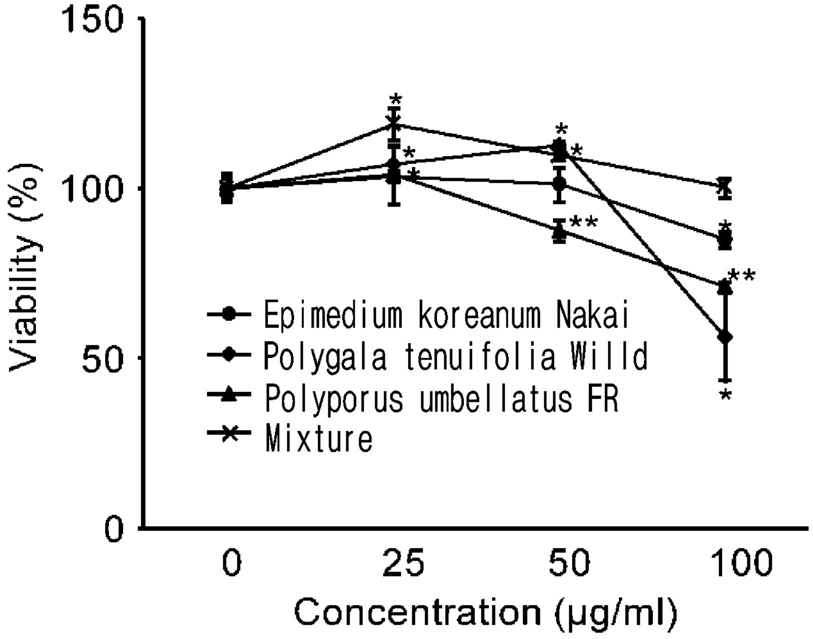
FIG. 1 is a graph showing the cytotoxicity of *Epimedium koreanum* Nakai, *Polygala tenuifolia* Willd, and *Polyporus umbellatus* Fries extracts and a mixture thereof according to the concentration through CCK-8 assay.

Hereinafter, the present invention is described in detail.

The embodiments of this invention can be modified in various other forms, and the scope of the present invention is not limited to the embodiments described below. It is well understood by those in the art who has the average knowledge on this field that the embodiments of the present invention are given to explain the present invention more precisely.

In addition, the "inclusion" of an element throughout the specification does not exclude other elements, but may include other elements, unless specifically stated otherwise.

In an aspect of the present invention, the present invention provides a pharmaceutical composition for the prevention or treatment of inflammatory diseases comprising *Epimedium koreanum* Nakai, *Polygala tenuifolia* Willd, and *Polyporus umbellatus* Fries extracts or a mixture thereof as an active ingredient.

The *Epimedium koreanum* Nakai, *Polygala tenuifolia* Willd, and *Polyporus umbellatus* Fries extracts of the present invention have an anti-inflammatory effect.

In an aspect of the present invention, anti-inflammatory is meant to include amelioration (relief of symptoms), treatment, inhibition or delay of the onset of an inflammatory disease defined below.

The inflammatory disease can be selected from the group consisting of inflammatory bowel disease, glomerulonephritis, inflammatory skin disease, retinitis, gastritis, hepatitis, enteritis, arthritis, tonsillitis, laryngopharyngitis, bronchitis, pneumonia, pancreatitis and nephritis.

In the present invention, to confirm the anti-inflammatory activity, the inhibitory activity of *Epimedium koreanum* Nakai, *Polygala tenuifolia* Willd, and *Polyporus umbellatus* Fries extracts on the production of nitric oxide (NO) and the expression of iNOS and COX-2 was evaluated at the cellular level. The extract of *Epimedium koreanum* Nakai, *Polygala tenuifolia* Willd, or *Polyporus umbellatus* Fries can be an extract prepared by extracting with water, alcohol, or a mixture thereof, and preferably can be an ethanol extract or a water extract. In addition, the ethanol extract can be an extract using 30% to 99% ethanol, 40% to 90% ethanol, 50% to 80% ethanol, or 60% to 75% ethanol.

In a specific embodiment of the present invention, the inventors analyzed the macrophage viability through CCK-8 assay to confirm the cytotoxicity of the *Epimedium koreanum* Nakai, *Polygala tenuifolia* Willd, and *Polyporus umbellatus* Fries extracts. As a result, the cytotoxicity was observed in the order of *Polygala tenuifolia* Willd, *Polyporus umbellatus* Fries, and *Epimedium koreanum* Nakai. However, it was confirmed that the cytotoxicity was inhibited when treated with a mixture of the three substances mixed in a constant ratio. The three substances can generally be treated in a mixture formulated in a ratio of 1:0.5~2:0.5~2, preferably in a ratio of 1:0.8~1.2:0.8~1.2, more preferably in a ratio of 1:0.9~1.1:0.9:1.1, and most preferably in a ratio of 1:1:1.

In addition, to confirm the anti-inflammatory effect of *Epimedium koreanum* Nakai, *Polygala tenuifolia* Willd, and *Polyporus umbellatus* Fries extracts, the present inventors analyzed the inhibition of nitric oxide (NO) production by *Epimedium koreanum* Nakai, *Polygala tenuifolia* Willd, and *Polyporus umbellatus* Fries extracts. As a result, *Epimedium koreanum* Nakai, *Polyporus umbellatus* Fries, and *Polygala tenuifolia* Willd showed high levels of nitric oxide inhibition in the order. In particular, as a result of converting the ratio of the reduced growth rate and nitric oxide inhibition due to cytotoxicity, a significant nitric oxide inhibitory effect was confirmed in a 1:1:1 mixture of the three substances.

In addition, to confirm the anti-inflammatory effects of *Epimedium koreanum* Nakai, *Polygala tenuifolia* Willd, and *Polyporus umbellatus* Fries extracts, the present inventors analyzed the degree of inhibition of iNOS and COX-2 expression by *Epimedium koreanum* Nakai, *Polygala tenuifolia* Willd, and *Polyporus umbellatus* Fries extracts. As a result, *Epimedium koreanum* Nakai showed very low levels of inhibition of iNOS and COX-2 expression, *Polygala tenuifolia* Willd effectively reduced iNOS, and *Polyporus umbellatus* Fries effectively reduced COX-2. Treatment with a 1:1:1 mixture of the three substances was the most effective in inhibiting COX-2 compared to treatment alone, and showed the same level of inhibition of iNOS as *Polyporus umbellatus* Fries.

Therefore, the *Epimedium koreanum* Nakai, *Polygala tenuifolia* Willd, and *Polyporus umbellatus* Fries extracts and the mixture thereof of the present invention can be effectively used as a pharmaceutical composition for the prevention or treatment of inflammatory diseases.

The pharmaceutical composition for the prevention or treatment of inflammatory diseases comprising the *Epimedium koreanum* Nakai, *Polygala tenuifolia* Willd, and *Polyporus umbellatus* Fries extracts of the present invention as an active ingredient can further include additional components. The composition can further include at least one of carriers, excipients, and diluents, for example, it can include at least one selected from the group consisting of lactose, dextrose, sucrose, sorbitol, mannitol, xylitol, erythritol, maltitol, starch, acacia gum, alginate, gelatin, calcium phosphate, calcium silicate, cellulose, methylcellulose, microcrystalline cellulose, polyvinylpyrrolidone, water, methylhydroxybenzoate, propylhydroxybenzoate, talc, magnesium stearate, and mineral oil.

The composition of the present invention can be administered orally or parenterally, and when administered parenterally, it is preferred that the composition be administered by external skin application or by intraperitoneal injection, intrarectal injection, subcutaneous injection, intravenous injection, intramuscular injection, or intrathoracic injection, but not always limited thereto.

The pharmaceutical composition for the prevention or treatment of inflammatory diseases can have various dosage forms, and can be formulated according to conventional methods in the form of pills, granules, tablets, capsules, suspensions, emulsions, syrups, aerosols, suppositories, and sterile injectable solutions. The pharmaceutical composition of the present invention can be prepared using generally used diluents or excipients such as fillers, extenders, binders, wetting agents, disintegrating agents and surfactants. Formulations for parenteral administration are sterilized aqueous solutions, water-insoluble excipients, suspensions, emulsions, lyophilized preparations and suppositories. Water insoluble excipients and suspensions can contain, in addition to the active compound or compounds, propylene glycol, polyethylene glycol, vegetable oil like olive oil, injectable ester like ethylolate, etc. Suppositories can contain, in addition to the active compound or compounds, witepsol, macrogol, tween 61, cacao butter, laurin butter, glycerogelatin, etc.

The preferred dosage of the composition of the present invention varies depending on the condition and weight of a patient, the severity of a disease, the drug type, the route and duration of administration, but can be appropriately determined by those skilled in the art. However, for a desired effect, the composition is preferably administered at 0.0001 to 1 g/kg per day, preferably 0.001 to 200 mg/kg, but not always limited thereto. The administration frequency is once a day or a few times a day. The dosage cannot limit the scope of the present invention by any means.

In another aspect of the present invention, the present invention provides a method for preparing a pharmaceutical composition for the prevention or treatment of inflammatory diseases, comprising the steps of extracting *Epimedium koreanum* Nakai, *Polygala tenuifolia* Willd, and *Polyporus umbellatus* Fries, concentrating the extracts, and lyophilizing the extracts.

The preparation of herbal medicine extracts of *Epimedium koreanum* Nakai, *Polygala tenuifolia* Willd and *Polyporus umbellatus* Fries was carried out according to the traditional decoction method. The entire process consists of extraction, concentration, and freeze-drying steps.

The extract of *Epimedium koreanum* Nakai, *Polygala tenuifolia* Willd, or *Polyporus umbellatus* Fries can be an extract prepared by extracting with water, alcohol, or a mixture thereof, and preferably can be an ethanol extract or a water extract. In addition, the ethanol extract can be an extract using 30% to 99% ethanol, 40% to 90% ethanol, 50% to 80% ethanol, or 60% to 75% ethanol.

The extraction solvent can be added in an amount of 1 to 50 times the weight (1 g) of *Epimedium koreanum* Nakai, *Polygala tenuifolia* Willd, and *Polyporus umbellatus* Fries used for extraction, in an amount of 3 to 40 times the weight (1 g) of *Epimedium koreanum* Nakai, *Polygala tenuifolia* Willd, and *Polyporus umbellatus* Fries used for extraction, in an amount of 5 to 30 times the weight (1 g) of *Epimedium koreanum* Nakai, *Polygala tenuifolia* Willd, and *Polyporus umbellatus* Fries used for extraction, in an amount of 7 to 20 times the weight (1 g) of *Epimedium koreanum* Nakai, *Polygala tenuifolia* Willd, and *Polyporus umbellatus* Fries used for extraction, and in an amount of 10 times the weight (1 g) of *Epimedium koreanum* Nakai, *Polygala tenuifolia* Willd, and *Polyporus umbellatus* Fries used for extraction.

The extraction method can be shaking extraction, Soxhlet extraction, or reflux extraction. At this time, the extraction temperature can be 50 to 150° C., preferably 60 to 140° C., more preferably 70 to 130° C., more preferably 80 to 120° C., more preferably 90 to 110° C., and most preferably 100° C., but not always limited thereto.

The concentration under reduced pressure is preferably performed by using a vacuum concentrator or a vacuum rotary evaporator, and the drying is preferably performed by reduced-pressurized drying, vacuum drying, boiling drying, spray drying, or freeze drying.

The ratio of the *Epimedium koreanum* Nakai, *Polygala tenuifolia* Willd, and *Polyporus umbellatus* Fries extracts is usually 1:0.5~2:0.5~2, preferably 1:0.8~1.2:0.8~1.2, more preferably 1:0.9~1.1:0.9:1.1, and most preferably 1:1:1.

In another aspect of the present invention, the present invention provides a health functional food for the prevention or amelioration of inflammatory diseases comprising *Epimedium koreanum* Nakai, *Polygala tenuifolia* Willd, *Polyporus umbellatus* Fries extracts and a mixture thereof as an active ingredient.

In this description, "health functional food" indicates the food produced with the supplement of such nutrients that are often lack in daily diet or raw materials or components having a useful function for human body. The health functional food refers to food that helps maintain the health of the human body, but not always limited thereto, and any general health food can be included.

The form and type of the health functional food is not specifically limited. Particularly, the health functional food can be in the form of tablets, capsules, powders, granules, liquids and pills. The health functional food can include various flavors, sweeteners, or natural carbohydrates as additional ingredients. The sweetener can be a natural or synthetic sweetener, and examples of the natural sweetener include thaumatin and stevia extract. On the other hand, examples of the synthetic sweetener include saccharin and aspartame. In addition, the natural carbohydrates can be monosaccharides, disaccharides, polysaccharides, oligosaccharides and sugar alcohols.

The *Epimedium koreanum* Nakai, *Polygala tenuifolia* Willd, and *Polyporus umbellatus* Fries extracts of the present invention can be added to food as is or used in combination with other foods or food components. At this time, the mixing ratio of active ingredients can be regulated according to the purpose of use. In general, the content of the extract in the health functional food can be 0.01 to 90 weight part of the total weight of the food. However, if long term administration is required for health and hygiene or regulating health condition, the content can be lower than the above but higher content can be accepted as well since the extract has been proved to be very safe.

The health functional food composition for the prevention or amelioration of inflammatory diseases comprising *Epimedium koreanum* Nakai, *Polygala tenuifolia* Willd, *Polyporus umbellatus* Fries extracts and a mixture thereof as an active ingredient can additionally include one or more effective ingredients having the same or similar function to the extract. For administration, it can be prepared by further including one or more carriers acceptable as food.

The health functional food composition for the prevention or amelioration of inflammatory diseases comprising *Epimedium koreanum Nakai, Polygala tenuifolia* Willd, *Polyporus umbellatus* Fries extracts and a mixture thereof as an active ingredient is preferably any one dosage form selected from the group consisting of beverages, pills, tablets, capsules, and powders, but not always limited thereto.

The ratio of the *Epimedium koreanum* Nakai, *Polygala tenuifolia* Willd, and *Polyporus umbellatus* Fries extracts is usually 1:0.5~2:0.5~2, preferably 1:0.8~1.2:0.8~1.2, more preferably 1:0.9~1.1:0.9:1.1, and most preferably 1:1:1.

The health functional food composition of the present invention can additionally include various flavors or natural carbohydrates, etc, like other beverages in addition to the extract. The natural carbohydrates above can be one of monosaccharides such as glucose and fructose, disaccharides such as maltose and sucrose, polysaccharides such as dextrin and cyclodextrin, and sugar alcohols such as xilytole, sorbitol and erythritol. Besides, natural sweetening agents (thaumatin, stevia extract, for example rebaudioside A, glycyrrhizin, etc.) and synthetic sweetening agents (saccharin, aspartame, etc.) can be included as a sweetening agent. The content of the natural carbohydrate is preferably 1-20 g and more preferably 5-12 g per 100 g of the composition of the present invention.

In addition to the ingredients mentioned above, the composition of the present invention can include in variety of nutrients, vitamins, minerals (electrolytes), flavors including natural flavors and synthetic flavors, coloring agents and extenders (cheese, chocolate, etc.), pectic acid and its salts, alginic acid and its salts, organic acid, protective colloidal viscosifiers, pH regulators, stabilizers, antiseptics, glycerin, alcohols, carbonators which used to be added to soda, etc.

Hereinafter, the present invention will be described in detail by the following examples and experimental examples.

However, the following examples and experimental examples are only for illustrating the present invention, and the contents of the present invention are not limited thereto.

Example 1: Preparation of *Epimedium koreanum* Nakai, *Polygala tenuifolia* Willd, and *Polyporus umbellatus* Fries Extracts Herbal medicine extracts were prepared according to the standard decoction preparation method in accordance with the Ministry of Food and Drug Safety Notice 2003-17, and Safety and Efficacy Review Regulations (2003). Purified water amount of 10 times the weight of the raw material drugs was added, and extraction was carried out at 80 to 100° C. for 2 to 3 hours until the extract was reduced to half its volume, and this point was considered the standard decoction. A product was considered equivalent if it contained at least 70% of the lower limit of the active ingredient or indicator ingredient of a daily supply, and the contained range was within ±30% of the center of the range.

Appropriate amounts of herbal medicines were purchased according to the extraction efficiency of each extract to be used in the test according to the standard decoction preparation method. Purified water 10 times the amount of herbal medicine was added and heated until the amount of water was reduced by half, followed by first filtration immediately. Thereafter, the filtrate was allowed to stand until it cooled down, and the solid components were removed by secondary filtration, and then the dried herbal extract was prepared using a lyophilizer.

The extract was freeze-dried to a powdered state, and distilled water was added to make it available at the proper concentration for use.

1. Standard Extract Preparation Method

The preparation of herbal medicine extracts of *Epimedium koreanum* Nakai, *Polygala tenuifolia* Willd and *Polyporus umbellatus* Fries was carried out according to the traditional decoction method. The entire process consists of extraction, concentration, and freeze-drying steps.

2. Extraction Process

The herb was washed with purified water corresponding to 2.5 times the sample, and the washed herb was put into an extractor and purified water of about 10 times the herb was added. After extraction at 100° C. and heating to reduce the extract by half, the extract was passed through a primary cartridge-type filter and the filtrate obtained was transferred to a buffer tank. The transferred hot water extract was left to cool overnight, and if necessary, it was forcibly cooled to prevent contamination from microorganisms or other factors due to extended exposure.

3. Concentration Process

The cooled extract in the buffer tank was subjected to secondary filtration using a housing-type filter, and then it was concentrated under reduced pressure using a continuous concentrator at 40-50° C. The concentration process was terminated when the total volume of the concentrate reached about 30 L, and the solid content in about 30 L was calculated based on an expected yield of 10-15%.

4. Freeze-Drying

The concentrate was aliquoted at approximately 2 L per tray and pre-frozen for 2 days in a deep freezer (freeze-drying: −70° C., 48H). The frozen trays were placed in a freeze dryer and dried for 72 hours at −70° C. and 0.06 mbar.

Example 1: Preparation of Mixture of *Epimedium koreanum* Nakai, *Polygala tenuifolia* Willd, and *Polyporus umbellatus* Fries Extracts A certain amount of each herbal extract was weighed on a scale and mixed with an excipient (sterile distilled water) to prepare a high dose (100 ug/ml) test substance as a suspension. This suspension was further diluted with sterile distilled water to prepare 50 and 25 ug/ml suspensions. For the preparation of the mixture, each extract was diluted in sterile distilled water and then mixed in a ratio of 1:0.5~2: 0.5~2 to confirm the anti-inflammatory effect.

In this experiment, the extraction was performed using hot water extraction. However, in addition to this method, the extraction can be performed by selecting any one of methods such as enfleurage, reflux-cooled extraction, solvent extraction method, steam distillation, ultrasonic extraction, elution, and expression.

Experimental Example 1: Cell Counting Kit-8 Assay (Cytotoxicity Test)

Raw 264.7 macrophages were seeded into a 96 well plate ($3\times10^4$ cells/well) and cultured for 24 hours, and then the plate was treated with the extract by concentration and cultured for 24 hours. After cultivation, CCK-8 was added to the plate, and after reacting for 1 hour, absorbance was measured at 450 nm using a microplate reader to evaluate cytotoxicity.

As shown in FIG. 1, as a result of CCK-8 assay performed to confirm the cytotoxicity of the natural substances, *Polygala tenuifolia* Willd showed the highest toxicity as the concentration increased, followed by *Polyporus umbellatus* Fries and *Epimedium koreanum* Nakai, and all three substances showed cytotoxicity. However, when a 1:1:1 mixture of the three substances was treated, the cytotoxicity induced by each substance was suppressed.

Experimental Example 2: Nitric Oxide (NO) Scavenging Activity

Raw 264.7 cells were pre-treated with the extract, and 1 hour later, treated with 1 μg/ml of LPS and cultured for 18 hours. The amount of NO produced in the culture medium was determined by measuring the absorbance at 560 nm using a griess reagent (1% sulfanilic acid: 1% napthylamine=1:1).

LPS is a substance that induces inflammation in animal cells, and when treated to macrophages, it promotes the secretion of nitric oxide, and a substances that alleviates inflammation inhibits the secretion of nitric oxide induced by LPS.

As shown in FIGS. 3 to 6, the natural substances used in the experiment showed high NO inhibition values in the order of the mixture, *Epimedium koreanum* Nakai, *Polyporus umbellatus* Fries, and *Polygala tenuifolia* Willd. However, when considering the ratio of the reduced growth rate due to cytotoxicity and the degree of nitric oxide inhibition, only the group treated with the mixture of the three substances showed an NO inhibition effect of 0.598 fold, and no significant effect was observed in the groups treated with the substances individually.

Experimental Example 3: Measurement of Apoptosis Signaling and Inflammatory Protein Expression Through Western Blot To confirm the changes in apoptosis signaling, Raw 264.7 cells were seeded into a 6-well plate at a concentration of $1.8\times10^5$ cells/mL, cultured for 24 hours, and then the samples were treated at a concentration of 100 μg/ml. After culturing for 24 hours, the cells were lysed with RIPA buffer and then centrifuged at 15,000 rpm for 20 minutes to extract proteins. The proteins quantified by BCA assay were separated by SDS-PAGE, and the separated proteins were transferred to a nitrocellulose membrane, followed by blocking in 5% skim milk/TTBS buffer for 1 hour. For confirming the changes in apoptosis signaling, blotting was performed overnight at 4° C. using anti-rabbit caspase 3 and anti-rabbit PARP antibodies as the primary antibodies. For measuring the inflammatory protein expression, blotting was performed overnight at 4° C. using anti-rabbit iNOS and anti-rabbit COX2 antibodies as the primary antibodies. As a secondary antibody, horseradish peroxidase-conjugated anti-rabbit IgG antibody was reacted for 1 hour at room temperature, and the band intensity was quantified along with identification of protein expression bands by ChemiDoc MP imaging system.

Apoptosis acts as a very important cause in cytotoxicity, and cytotoxicity can be verified through caspase3 processing and PARP cleavage.

Figure 2:
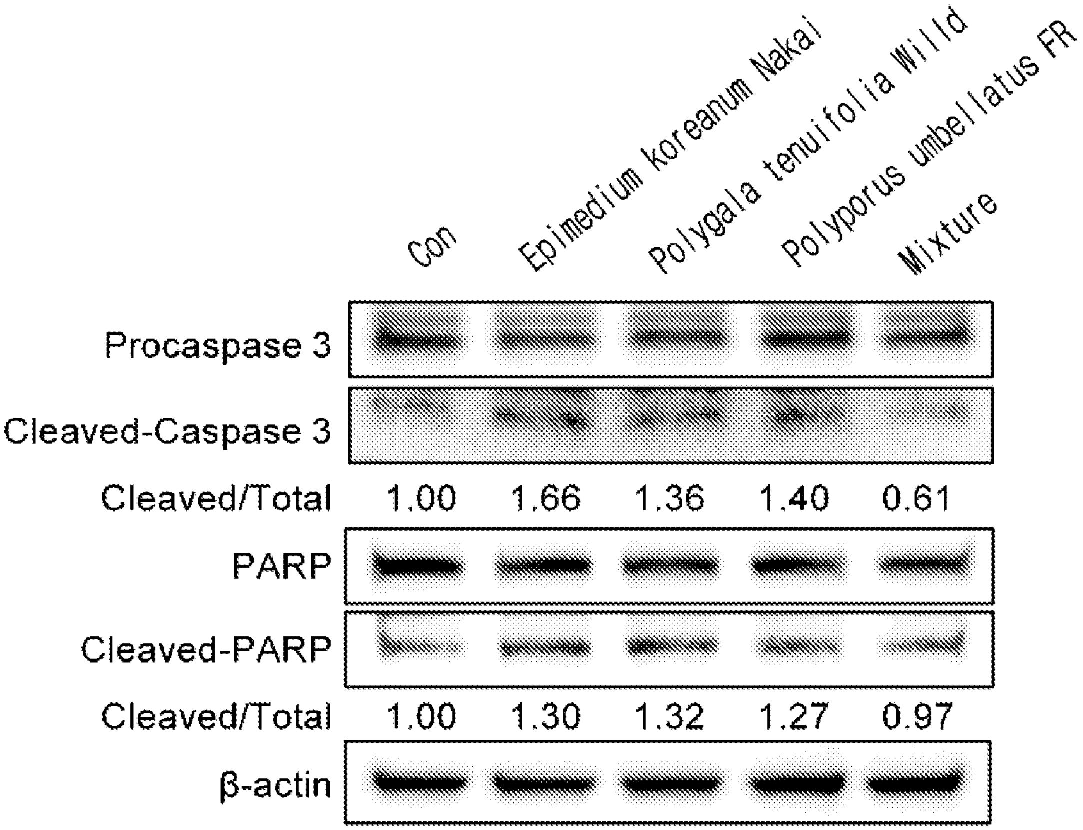
FIG. 2 is a diagram showing the cytotoxicity of *Epimedium koreanum* Nakai, *Polygala tenuifolia* Willd, and *Polyporus umbellatus* Fries extracts and a mixture thereof through apoptosis.
Figure 3:
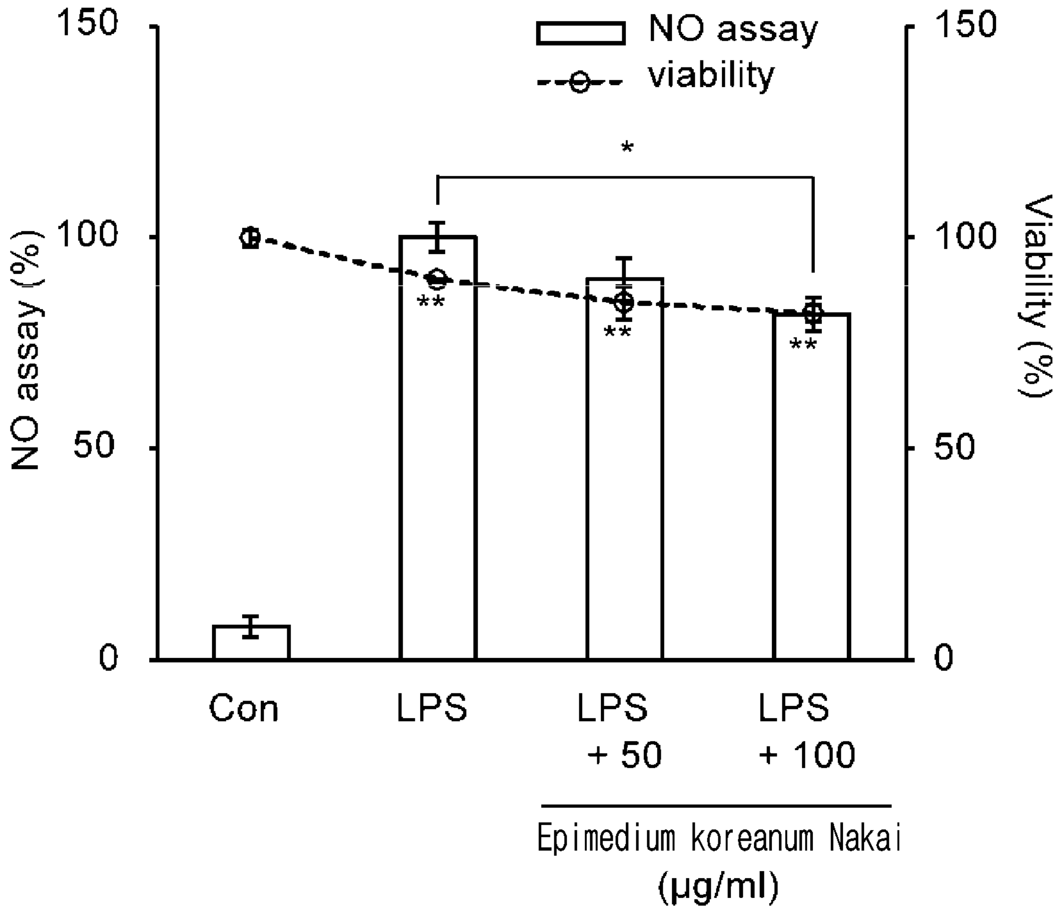
FIG. 3 is a graph showing the degree of inhibition of NO secreted upon LPS treatment to macrophages when treated with *Epimedium koreanum* Nakai extract through NO assay.
Figure 4:
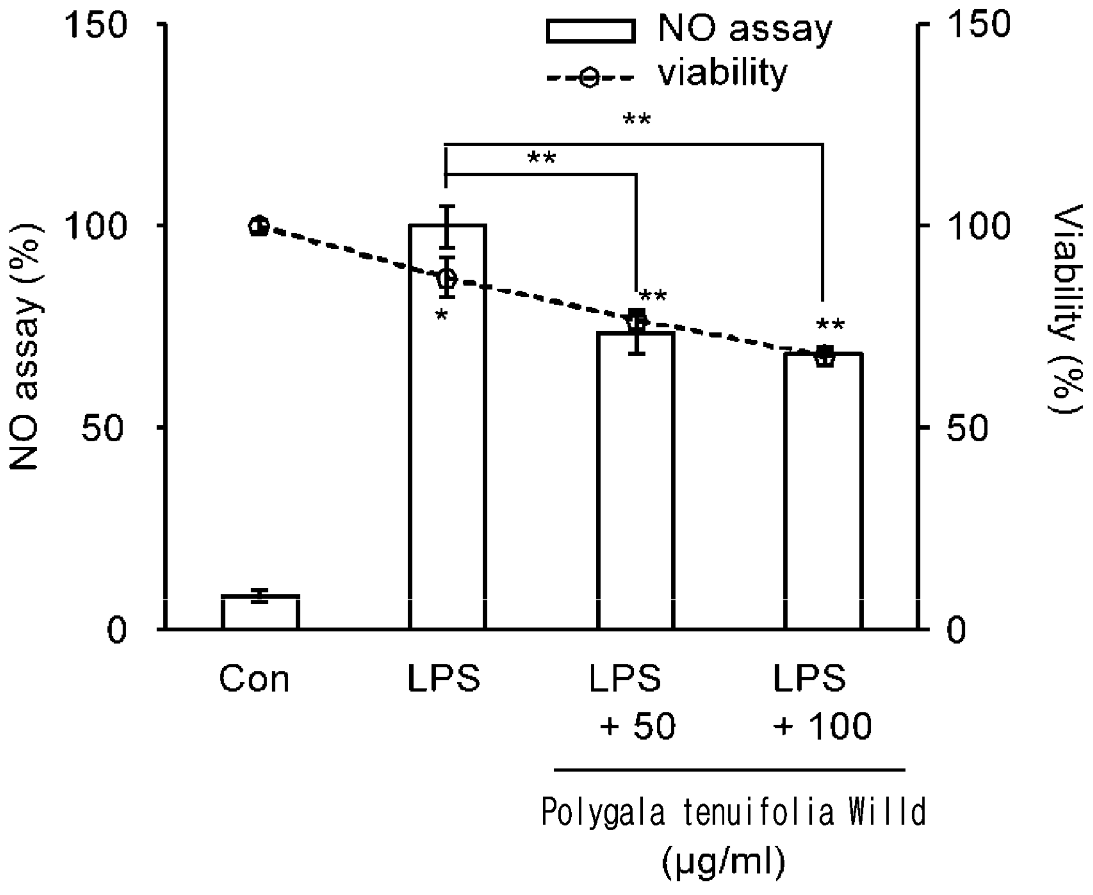
FIG. 4 is a graph showing the degree of inhibition of NO secreted upon LPS treatment to macrophages when treated with *Polygala tenuifolia* Willd extract through NO assay.
Figure 5:
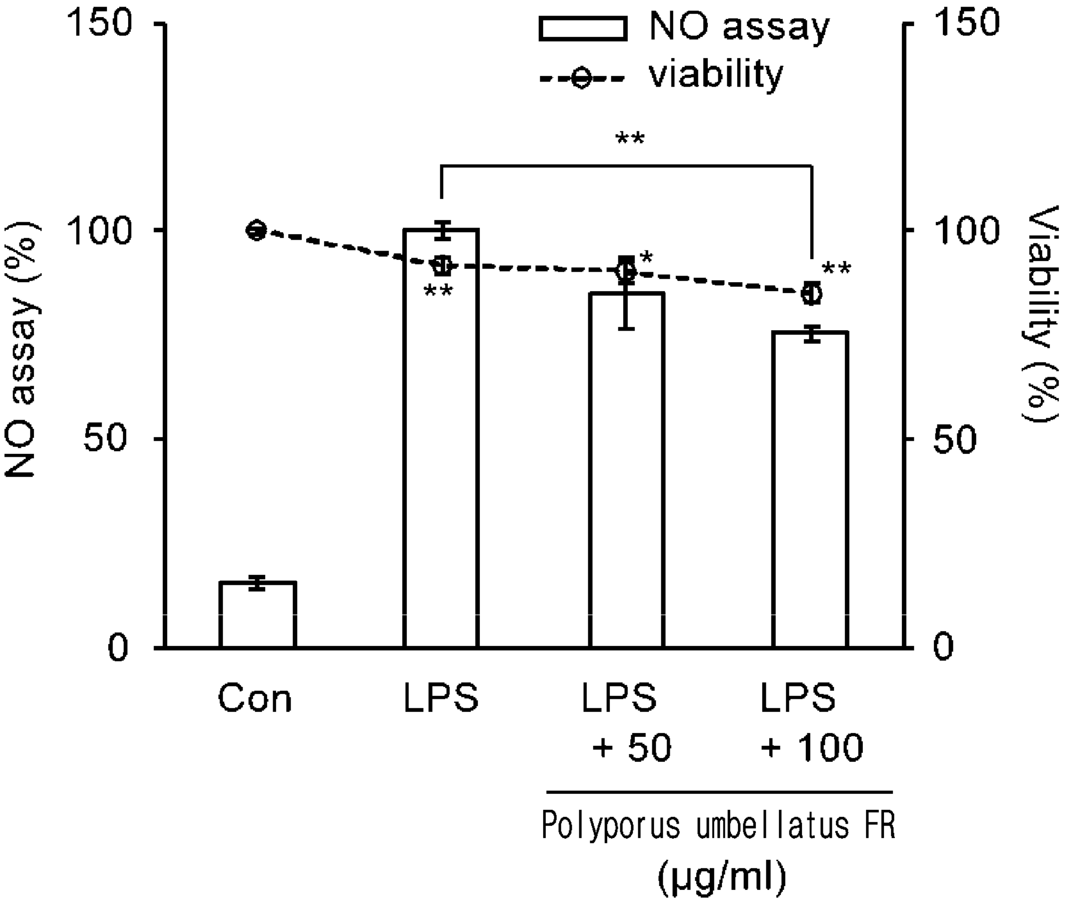
FIG. 5 is a graph showing the degree of inhibition of NO secreted upon LPS treatment to macrophages when treated with *Polyporus umbellatus* Fries extract through NO assay.
Figure 6:
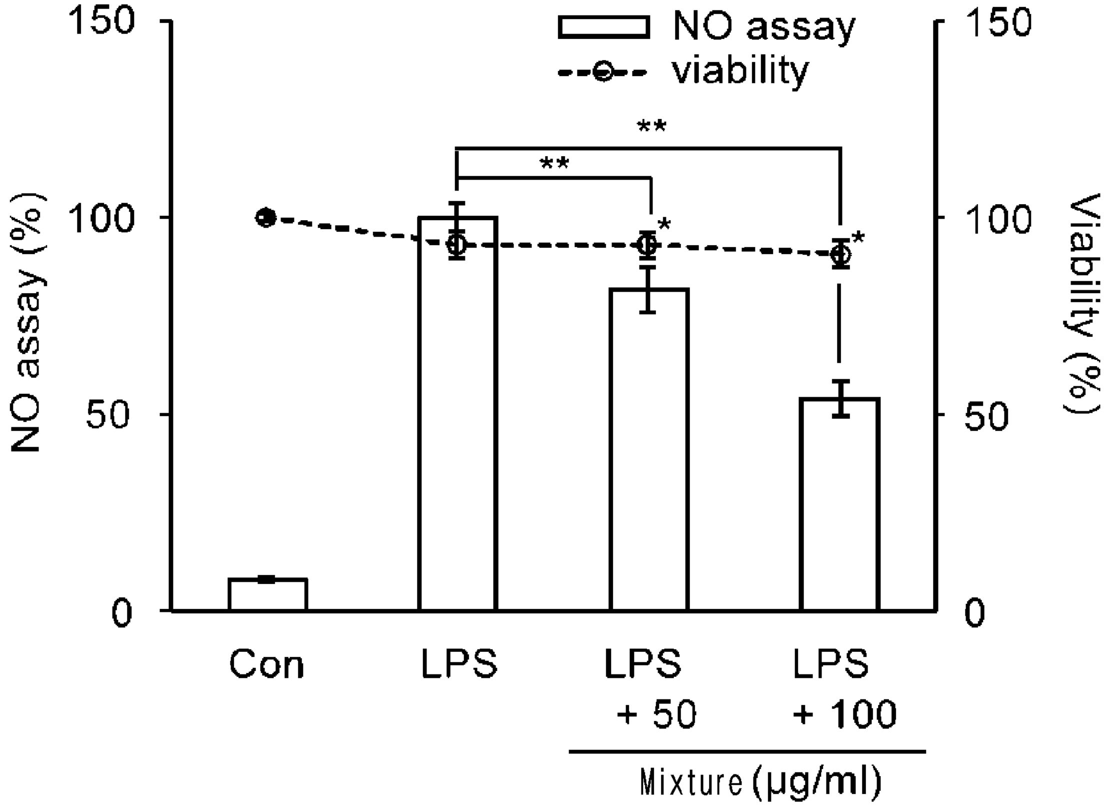
FIG. 6 is a graph showing the degree of inhibition of NO secreted upon LPS treatment to macrophages when treated with a mixture of *Epimedium koreanum* Nakai, *Polygala tenuifolia* Willd, and *Polyporus umbellatus* Fries through NO assay.

As shown in FIG. 2, each substance showing cytotoxicity induced apoptosis by inducing cleavage of caspase 3 and PARP, and no increase in apoptosis signal was observed in the group treated with the mixture that did not show toxicity, which was the same as the CCK-8 result measuring cytotoxicity in <Experimental Example 1>.

When an inflammatory response is induced by LPS, the expression of iNOS and COX2 is increased. Substances that induce an anti-inflammatory response suppress the expression of iNOS and COX2 induced by LPS, and through this, the signaling mechanism for the intracellular inflammation suppression effect can be confirmed.

Figure 7:
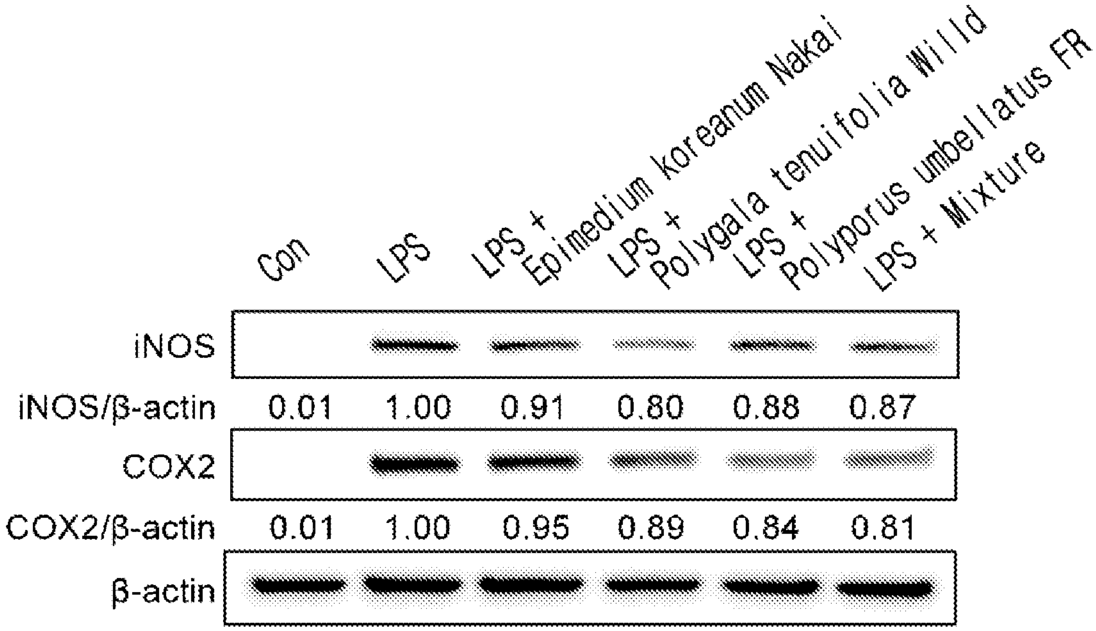
FIG. 7 is a diagram showing the degree of inhibition of iNOS and COX2 expressed upon LPS treatment when treated with *Epimedium koreanum* Nakai, *Polygala tenuifolia* Willd, and *Polyporus umbellatus* Fries extracts and a mixture thereof.

As shown in FIG. 7, *Epimedium koreanum* Nakai showed very low levels of inhibition of iNOS and COX2 expression, while *Polygala tenuifolia* Willd reduced iNOS, and *Polyporus umbellatus* Fries effectively reduced COX2. The mixture inhibited COX2 most effectively compared to the individual substances, and showed the same level of iNOS inhibitory effect as *Polyporus umbellatus* Fries.

All three natural substances used in the experiment were confirmed to have anti-inflammatory efficacy through the inhibition of iNOS and COX2 expression at the cellular level, but they strongly induced cytotoxicity. However, when the three substances were mixed, the cytotoxicity of each substance was reduced, and at the same time, a stable anti-inflammatory signaling mechanism was maintained. Therefore, a mixture of 1:1:1 is suitable for suppressing the cytotoxic side effects caused by *Epimedium koreanum Nakai, Polygala tenuifolia* Willd, and *Polyporus umbellatus* Fries and for use as an effective anti-inflammatory substance.

Therefore, the 1:1:1 mixture of *Epimedium koreanum* Nakai, *Polygala tenuifolia* Willd, and *Polyporus umbellatus* Fries can be effectively used as an anti-inflammatory composition because it has lower cytotoxic side effects, and exhibits high nitric oxide production inhibitory effect and iNOS and COX2 inhibitory effects.

INDUSTRIAL APPLICABILITY

The extracts and mixture provided in an aspect of the present invention exhibit a high inhibitory effect against nitric oxide and a suppressive effect against the expression of iNOS and COX2 and thus can be advantageously used as an anti-inflammatory composition.

The invention claimed is:

1. A method of treating inflammatory bowel disease, comprising administering to a subject in need thereof a pharmaceutical composition comprising active ingredients, wherein the active ingredients consist of a mixture of water extracts of *Epimedium koreanum* Nakai, *Polygala tenuifolia* Willd, and *Polyporus umbellatus* Fries, wherein the water extract of *Epimedium koreanum* Nakai, water extract of *Polygala tenuifolia* Willd, and water extract of *Polyporus umbellatus* Fries are present in the mixture at a weight ratio of 1:0.5~2:0.5~2.

2. The method of treating an inflammatory bowel disease according to claim 1, wherein the water extract of *Epimedium koreanum* Nakai, water extract of *Polygala tenuifolia* Willd, and water extract of *Polyporus umbellatus* Fries are present in the mixture at a weight ratio of 1:1:1.

3. The method of treating an inflammatory bowel disease according to claim 1, wherein each of the water extracts is prepared by extracting the corresponding herbal material with water at 80 to 100° C. for 2 to 3 hours.

4. The method of treating an inflammatory bowel disease according to claim 1, wherein each of the water extract of *Epimedium koreanu*m Nakai, water extract of *Polygala tenuifolia* Willd, and water extract of *Polyporus umbellatus* Fries suppresses the production of nitric oxide (NO).

5. The method of treating an inflammatory bowel disease according to claim 1, wherein each of the water extract of *Epimedium koreanu*m Nakai, water extract of *Polygala tenuifolia* Willd, and water extract of *Polyporus umbellatus* Fries inhibits the expression of iNOS.

6. The method of treating an inflammatory bowel disease according to claim 1, wherein each of the water extract of *Epimedium koreanu*m Nakai, water extract of *Polygala tenuifolia* Willd, and water extract of *Polyporus umbellatus* Fries inhibits the expression of COX-2.

7. A method of ameliorating inflammatory bowel disease, comprising administering to a subject in need thereof a health functional food composition comprising active ingredients, wherein the active ingredients consist of a mixture of water extracts of *Epimedium koreanu*m Nakai, *Polygala tenuifolia* Willd, and *Polyporus umbellatus* Fries, wherein the water extract of *Epimedium koreanu*m Nakai, water extract of *Polygala tenuifolia* Willd, and water extract of *Polyporus umbellatus* Fries are present in the mixture at a weight ratio of 1:0.5~2:0.5~2.

8. The method of ameliorating an inflammatory bowel disease according to claim 7, wherein the water extract of *Epimedium koreanu*m Nakai, water extract of *Polygala tenuifolia* Willd, and water extract of *Polyporus umbellatus* Fries are present in the mixture at a weight ratio of 1:1:1.

9. The method of ameliorating an inflammatory bowel disease according to claim 7, wherein each of the water extracts is prepared by extracting the corresponding herbal material with water at 80 to 100° C. for 2 to 3 hours.

10. The method of treating an inflammatory bowel disease according to claim 1, wherein the inflammatory bowel disease is mediated by NO.

11. The method of treating an inflammatory bowel disease according to claim 1, wherein the inflammatory bowel disease has increased expression of an inflammatory protein.

12. The method of treating an inflammatory bowel disease according to claim 11, wherein the inflammatory protein is iNOS or COX-2.

* * * * *